United States Patent [19]

Feucht

[11] Patent Number: 4,754,757
[45] Date of Patent: Jul. 5, 1988

[54] METHOD AND APPARATUS FOR MONITORING THE SURFACE CONTACT OF A NEUTRAL ELECTRODE OF A HF-SURGICAL APPARATUS

[76] Inventor: Peter Feucht, Feurigstr. 54, 1000 Berlin 62, Fed. Rep. of Germany

[21] Appl. No.: 929,561

[22] Filed: Nov. 10, 1986

[30] Foreign Application Priority Data

Dec. 16, 1985 [DE] Fed. Rep. of Germany ....... 3544443

[51] Int. Cl.$^4$ ............................................. A61B 17/39
[52] U.S. Cl. .................................. 128/303.13; 128/908
[58] Field of Search ...................... 128/303.13, 303.14, 128/303.17, 908

[56] References Cited

U.S. PATENT DOCUMENTS

| | | | |
|---|---|---|---|
| 3,683,923 | 8/1972 | Anderson | 128/303.14 |
| 3,897,787 | 8/1975 | Ikuno et al. | 128/303.14 |
| 4,200,105 | 4/1980 | Gonsend | 128/303.14 |
| 4,231,372 | 11/1980 | Newton | 128/303.14 |
| 4,384,582 | 5/1983 | Watt | 128/303.13 |

FOREIGN PATENT DOCUMENTS

| | | |
|---|---|---|
| 2657702 | 6/1977 | Fed. Rep. of Germany . |
| 2849422 | 5/1979 | Fed. Rep. of Germany . |
| 2516782 | 5/1983 | France . |

OTHER PUBLICATIONS

Siemens Publication "Kleine Einfuehrung in die Electrochirurgie", pp. 3–31.
tkb Pamphlet "Sichertheitstechnische Anforderungen", pp. 106–108.

Primary Examiner—Lee S. Cohen
Attorney, Agent, or Firm—Lawrence C. Edelman

[57] ABSTRACT

The HF-current generator of an electrosurgical apparatus has one terminal connected to an active electrode and an additional terminal connected to a neutral electrode. The neutral electrode consists of at least two partial electrodes which are individually connected via connecting leads to respective current meters for measuing the partial currents in the respective connecting leads. The output side of the current meters are connected to a logic element that is provided for combining the partial currents and which provides a logic signal that is a function of their combination. A ratio generator is preferably provided as the logic element to develop a logic signal that is a function of the ratio of the partial currents. A comparator for comparing the logic signal with pre-set limit value is associated with the logic element. The output signal of the comparator is used as an alarm signal to actuate an alarm or a protective means for a patient in contact with the neutral electrode.

23 Claims, 2 Drawing Sheets

METHOD AND APPARATUS FOR MONITORING THE SURFACE CONTACT OF A NEUTRAL ELECTRODE OF A HF-SURGICAL APPARATUS

BACKGROUND OF THE INVENTION

1. Field of the Invention

The present invention relates to a method and apparatus for monitoring the surface contact between a neutral electrode of a high-frequency (HF) surgical apparatus and a patient wherein the neutral electrode is split into at least two partial electrodes and wherein a comparison dependent alarm signal is generated.

2. Description of the Prior Art

HF-surgical apparatus is particularly useful for the stanching of blood during surgery. The oozing of blood is simply, quickly and safely stopped by the application of a spherical or flat electrode. Smaller vessels are grasped with a clamp and contacted with an active electrode; the vessel is sealed by coagulation and simultaneously bonded to the immediate area. The clamp may then be immediately removed. Thus, a ligature is no longer required in the case of small and medium sized vessels. (see Publication "Kleine Einfuehrung in die Elektrochirugie", published and available from Siemens AG, Erlangen, Federal Republic of Germany, Order No. ME 3990/1231, Pages 1 through 31).

The HF-current of a HF-surgical apparatus is normally a current flowing alternately in two directions. However, for the purpose of simplifying the following description, this HF-current will be treated as a direct current which flows from the HF-surgical apparatus, through a switch actuated by the operator to the active electrode, from there through the body of the patient to the neutral electrode, and from the neutral electrode back to the HF-signal apparatus.

In the ideal case the HF-current will flow at full intensity from the active electrode, through the patient and the neutral electrode and then back to the HF-surgical apparatus. In practice however, on occasion, so called "undesirable burns" result to the patient. The present invention deals with fault currents which flow through areas of limited or incomplete surface contact and lead to burns in these areas. These burns may occur at points where accessories are connected to the patient, but also at points where the neutral electrode does not make sufficiently close surface contact with the patient. The resulting burns may reach a degree where they become life threatening to the patient. The pamphlet "tkb" entitled "Sicherheitstechnische Anforderungen ("Technical Safety Requirements"), Pages 106 through 108), describes the various risks involved in the use of a HF-surgical apparatus having an isolated neutral electrode.

It is well known that patient safety is enhanced by dividing the neutral electrode into two partial electrodes. In such an arrangement, an auxiliary or measuring current is conducted from a measuring current source to one of the partial electrodes. From there, the current is conducted through the patient to the other one of the partial electrodes, and finally back to the measuring current source where it is monitored. When this current circuit is completed, it is established with certainty that essentially the total surface of each of the partial electrodes is in close contact with the patient and that the actual HF-working current may be applied. Although such a separated neutral electrode does indeed make it possible to determine whether proper contact is being made, it requires the application of a special auxiliary or measuring current.

As already mentioned, every effort must be made to avoid burns to the patient by the neutral electrode during HF-surgery. For the problem under consideration here, i.e., the risk of burns resulting from incomplete (reduced) surface area contact, an alarm signal is to be produced and/or safety means simultaneously actuated. Stated another way: Assurance against burns during the use of present day HF-surgical apparatus would be greatly enhanced if the surface area of the neutral electrode which is in close contact with the patient is adequately large. This will insure that the current density does not exceed a specified critical value. It is of importance, therefore, to monitor the totality of contact or the degree of surface area contact.

One method and circuit arrangement for measuring electrode contact area in electrosurgery devices is known from U.S. Pat. No. 4,200,104 (corresponding to DE-OS No. 2849422). In this known circuit arrangement, the neutral electrode is divided into two partial electrodes. The extent of the surface contact between the two partial electrodes and the patient is measured through an arrangement which directly determines the capacitance between the two partial electrodes. The capacitance measuring device includes a circuit for applying a signal between these two electrically conducting contact elements. The capacitance measuring device also includes means for determining whether the surface contact between the patient-double electrode and the patient exceeds a pre-determined value corresponding to the safe operation of the HF-surgical apparatus. It is known that the procedure for making the capacitance measurements involves difficulties and uncertainties and, moreover, requires a signal generator for providing the signal used for the capacitance measurement.

An object of the present invention is to provide a method and protective circuit arrangement which will make it possible to determine, with a high degree of safety, whether the neutral electrode of a HF-surgical apparatus contacts the patient with an adequately large surface area, without the necessity of making a capacitance measurement.

SUMMARY OF THE INVENTION

In accordance with the invention, this object is achieved by exciting the active electrode with a HF-current, measuring and combining values of the partial currents entering the partial electrodes and generating an alarm signal which depends upon a comparison of this combination of the partial currents with a pre-set limit value.

A circuit arrangement for accomplishing this method comprises a HF-generator having a terminal for the active electrode and an additional terminal for the neutral electrode, a comparator element, and a neutral electrode consisting of at least two partial electrodes. Each partial electrode may be connected, via a current meter provided for measuring a partial current, to the additional terminal for the neutral electrode. The output of each of the current meters is connected to a logic element provided for combining the partial currents, and which provides an output signal determined by the combination. The logic element is coupled to a comparator which is provided to compare the logic signal with a pre-set limit value for developing the alarm signal.

The fact that this method and this circuit arrangement can be fabricated with relatively simple and inexpensive components is considered a distinct advantage. Moreover it is to be stressed that this method and circuit arrangement do not require the measurement of capacitance or the application of an auxiliary signal to the partial electrodes.

The method proposed here, therefore, relies upon a measurement of the HF-partial currents of a sub-divided neutral electrode and the development of an alarm signal via a logic operation, such as a ratio of the partial currents. Thus, two, three or an even greater number of partial electrodes may be employed, all of which will preferably have the same surface area. If as a result of the logical combination of the measured signals, it is established that there is an approximate equality of current distribution to the partial electrodes, burns to the patient may be ruled out and the alarm signal is not activated. On the other hand, alarm and safety means are brought into action if the HF-partial currents and their logical combination indicate that one of the partial currents exceeds a specified value.

Other features and advantages of the invention will be apparent from the following description of the preferred embodiments and from the claims.

For a fuller understanding of the present invention, reference should now be made to the following description of the preferred embodiments of the invention and to the accompanying drawings.

DETAILED DESCRIPTION OF THE PREFERRED EMBODIMENTS

Figure 1:
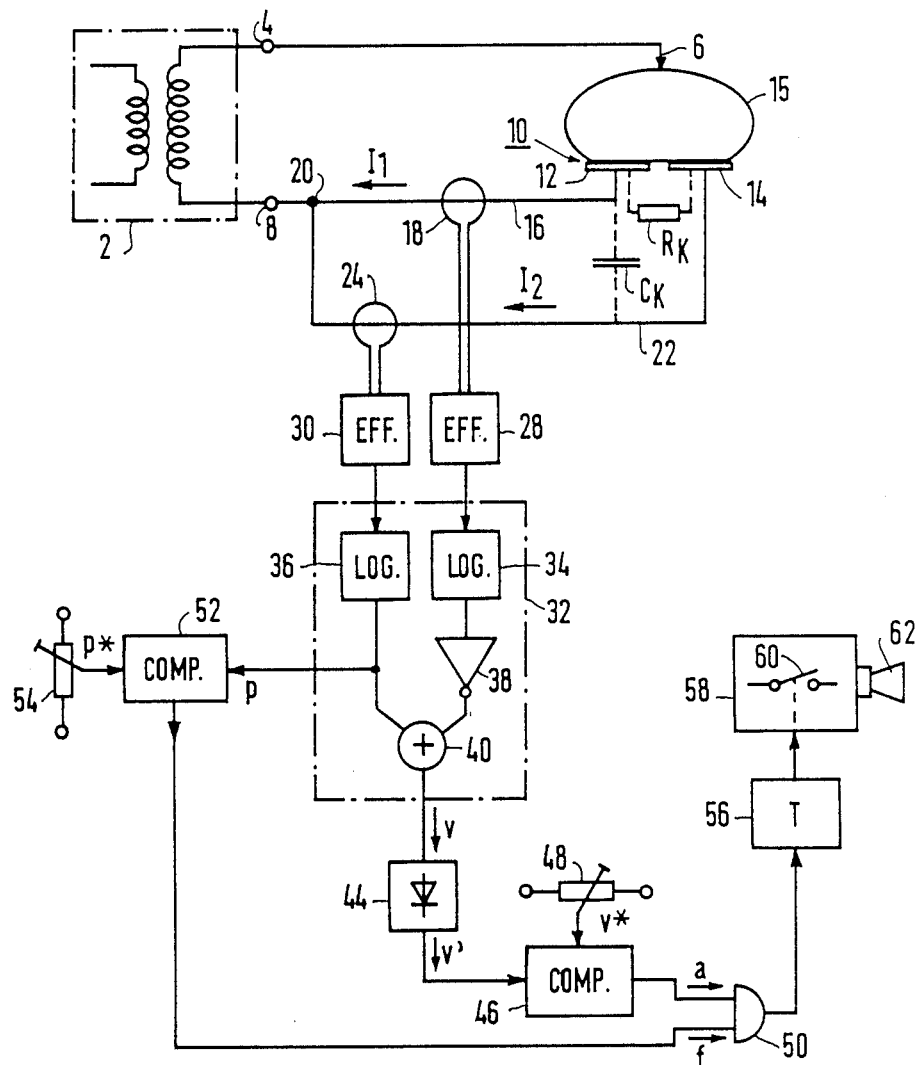
FIG. 1 illustrates a HF-surgical apparatus with a circuit arrangement for monitoring the neutral electrode in accordance with the invention.

FIG. 1 comprises a HF-surgical apparatus including a HF-generator 2 having a terminal 4 for the active electrode and an additional terminal 8 for the neutral electrode 10. In the present case neutral electrode 10 is subdivided into two partial electrodes 12 and 14. During a surgical procedure, neutral electrode 10 is attached to the patient 15 in the usual manner (e.g., to the upper thigh). During the procedure, the surgeon manipulates active electrode 6 and performs directed coagulations. The short circuit resistance between the partial electrodes 12, 14 is indicated by the resistance symbol Rk and the short circuit capacitance by the symbol Ck.

The first partial electrode 12 is connected via a lead 16 and a first current meter 18 to a terminal point 20. Correspondingly, the second partial electrode 14 is connected via a lead 22 and a second current meter 24 to the same terminal point 20. Terminal point 20 is connected to terminal 8 of HF-generator 2. Partial electrodes 12, 14 will preferably have the same surface area and be of identical construction. Current meters 18, 24 will preferably also be of the same construction and they are specifically shown as current transformers in the present instance. Current meters 18, 24 serve as means for measuring the partial currents I1 and I2 in leads 16 and 22, respectively.

Current meters 18, 24 are followed in the circuit by components 28, 30, respectively, for the development of the effective value of the respective partial currents I1, I2. The outputs of components 28, 30 are connected to a logic element 32 for combining the effective values of partial currents I1, I2 and outputting a logic signal v which is a function of their combination. In the present embodiment, logic element 32 is designed as a ratio device which develops the logarithm of the logic signal v that is a function of the ratio I1/I2 of the two partial currents. For this purpose components 28, 30 are followed in the circuit by the logarithm generating elements 34, 36, respectively. The logarithms of the effective values of the two partial currents are next subtracted one from the other. This occurs through an inverter element 38 which follows logarithm generating element 34 in the circuit, and a summing element 40, to which are connected both the output signal of logarithm generating element 36 as well as the output signal of inverter element 38. The output signal of summing element 40 is the logic signal v. It is a function of the difference of the logarithms of the effective values of the two partial currents and can assume either positive or negative polarity. Components 38, 40 are therefore to be considered as subtraction or difference elements.

The positive or negative logic signal is subjected to further processing. For this purpose a rectifier 44 is connected to the output of logic element 32. Its output signal v' is input to a comparator 46. Comparator 46 is provided to compare the rectified logic signal v' with a pre-set limit value v*. Limit value v* may be entered via a threshold control 48, which is shown, for example, as a potentiometer. The output signal of comparator 46 is used as alarm signal a, and is input to an AND-logic element 50. Alarm signal a serves to actuate an alarm and/or safety means during an inequality of the two partial currents I1 and I2 beyond the rated value, for it may then be assumed that one of partial electrodes 12, 14 is not in complete contact with the skin of the patient 15.

In addition to alarm signal a, an enable signal f is also input to AND-logic element 50. Enable signal f is derived from a level comparator circuit. It is provided as a means of level monitoring, and comprises a level comparator 52 responsive to a measured value of one of current meters 18, 24, (in the present case from current meter 24, which is a function of partial current I2). In particular, in the present case, the input of level comparator 52 is connected to the output of logarithm generating element 36. Level comparator 52, has a pre-set level value p*. A potentiometer 54 acts as a source from which the level value p* may be acquired. Upon exceeding the level value p*, through the input of the logarithm of the effective value of partial current I2, the enable signal f is generated. Enable signal f is applied to AND-element 50 to enable the conduction of alarm signal a for further processing. Thus during "sub-level" periods, i.e., when no situations critical to the patient arise and possible malfunctions of the logarithm generators may occur, monitoring of logic signal v is inoperative.

The output of AND-element 50 is preferably connected to a timing element 56 (T). Timing element 56 may be provided to produce a delayed response. Alternatively, it may also serve to provide a pre-set dead time for the shut-down of Hf-generator 2, upon actuation of alarm signal a (i.e.: to make available an increase in the shut-down period).

The output of AND-element 50 is coupled through timing element 56 to an alarm system 58. This alarm system serves either to cut-off or reduce the HF-current I delivered by active electrode 6 and/or to activate an audible or visual alarm by unit 62. This is symbolized by the switch 60 within box 58 indicating the alarm system. The alarm system is thus actuated, that is, it provides an alarm and/or it carries out a safety procedure, first, when a significant inequality in partial currents I1, I2 is detected (whereby the value of the pre-set limit value v* is exceeded, that is upon exceeding the "threshold of the inequality") and second, when an adequate level of one of partial currents I1, I2 is presented, the limit value of which has been pre-set by limit value p*.

In principle simple resistances may be employed for current measurement. However, so called feed-through current transformers with a toroidal core are preferred for the acquisition of partial currents I1, I2. These have, for example, a bandwidth from 10 kHz to 10 MHz. Transformers have the advantage that a small voltage on the primary side is readily converted to a relatively high voltage on the secondary side. The insertion resistance is quite small, for example, in the order of 0.1 Ohm. A further advantage derives from the separation of potentials and a reduced coupling capacitance. For example, feed-through current transformers may be constructed which, with a partial current of 1 amp, produce a voltage of 1000 mV into 10 ohms. This makes the circuit relatively insensitive to coupling capacitances Ck and coupling resistances Rk between partial electrodes 12, 14.

In principle, the difference of two partial currents I1, I2 might also be generated in logic element 32 (even with the use of additional sub-electrodes). In contrast to the generation of such absolute differences, the generation of the ratio employed here has the advantage that the circuitry is independent of the measured current intensities I1, I2 over a wide range. In other words, even with relatively low currents I1, I2 . . . , that is, when the power output of the HF-generator is not yet fully employed, the monitoring system is still relatively sensitive.

This is equally true in relation to a construction in which, as an example, the neutral electrode consists of ten partial electrodes, in which each partial electrode is monitored for an absolute power output of say 50 Watts. If the partial current of one of these electrodes exceeds a pre-set limit value, there is a risk of burning, and alarm and/or safety means are actuated.

The following comment is in order in connection with the measurement of the effective values by means of components 28, 30. Since highly unusual waveshapes are dealt with in HF-surgery, the generation of true effective values is adopted. In practice then, a power acquisition means independent of the waveshape is employed. The alternative to this approach, i.e. peak value rectification is, of course, also possible. Favoring effective value measurement however, is the fact that integrated circuits operating in the megahertz (MHz) region are commercially available. A solution involving discrete components would not be much more economical, and in relatively high volume, problems may result.

Logarithm generation by means of elements 34, 36 and the associated generation of differences through components 38, 40 serve, as shown, to develop the ratio or quotient of the two partial currents I1, I2. In this way the quotient is held within fixed limits, for example within a dynamic range of 30 dB, practically independent of the power. With the help of a supplemental operational amplifier, the integrated circuit implementation mentioned above would have the capability of generating the logarithm.

Figure 2:
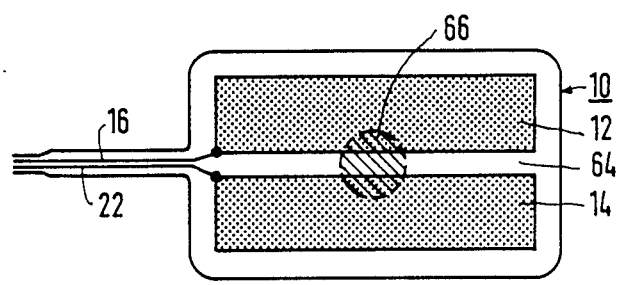
FIG. 2 illustrates a double sub-divided neutral electrode for use in a monitoring circuit in accordance with FIG. 1.

FIG. 2 shows a two part neutral electrode 10 which can be employed with the monitoring circuit according to FIG. 1. The two electrodes 12 and 14 are of approximately the same size and of rectangular design. They consist essentially of an electrically conducting mesh and are placed upon an electrically insulated but flexible backing particularly an insulating rubber. The dividing line 64, between the two partial electrodes 12, 14 is of linear shape. Sub-electrodes 12 and 14 have a relatively short separation from the dividing line 64.

With the help of the two part neutral electrodes 10, it is therefore possible to determine through measurement and comparison of the partial currents I1 and/or I2 in the two leads 16 and/or 22, whether an approximately equal division of the two currents has been achieved. With this established, burns to the patient 15 are avoided with a high degree of safety. But even in this case, burns may not be totally ruled out, because very small regions or contact surfaces 66 (which are shown cross-hatched, and which lie on the dividing line 64 of the two partial electrodes 12, 14) also produce an equal current loading in supply lines 16, 22. A practically dot shaped contact region 66, along dividing line 64 would therefore, under some circumstances, prevent the detection of improper contact of the neutral electrode 10 in the circuit arrangement shown in FIG. 1.

Figure 3:
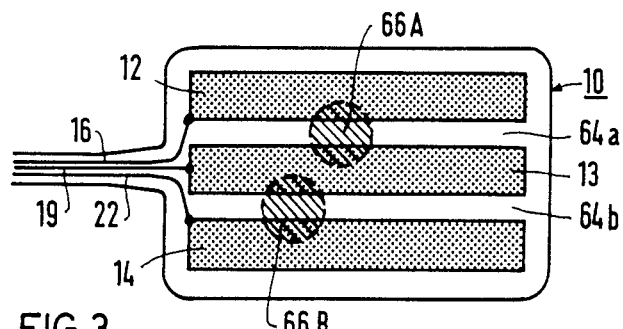
FIG. 3 illustrates a triple sub-divided neutral electrode that is preferred because of enhanced safety.

In this regard, in order to establish a still greater degree of safety, a triple sub-divided neutral electrode 10 may be used as shown in FIG. 3. Electrode 10 consists of three narrow, rectangular partial electrodes 12, 13, 14 having equal surface areas, which are again in the form of conducting meshes attached to a common backing and provided with respective connecting leads 16, 19, 22. As opposed to double sub-divided electrode 10 shown in FIG. 2, triple sub-divided neutral electrod 10, provides at least double again the degree of safety against burns since, in order to lead to a situation where an alarm is enabled, at least two equal contact surfaces 66A and 66B (here again shown by circles) must occur concurrently. A situation in which the two quasi spot-like contact regions 66A, 66B occur at the same time, and in which they occur exactly on one of the dividing lines 64a and 64b, is held to be highly improbable.

Of course, the triple sub-division of electrode 10 may also be done in the other direction relative to the extended length. This leads to a transverse separation which represents an especially safe variation.

Figure 4:
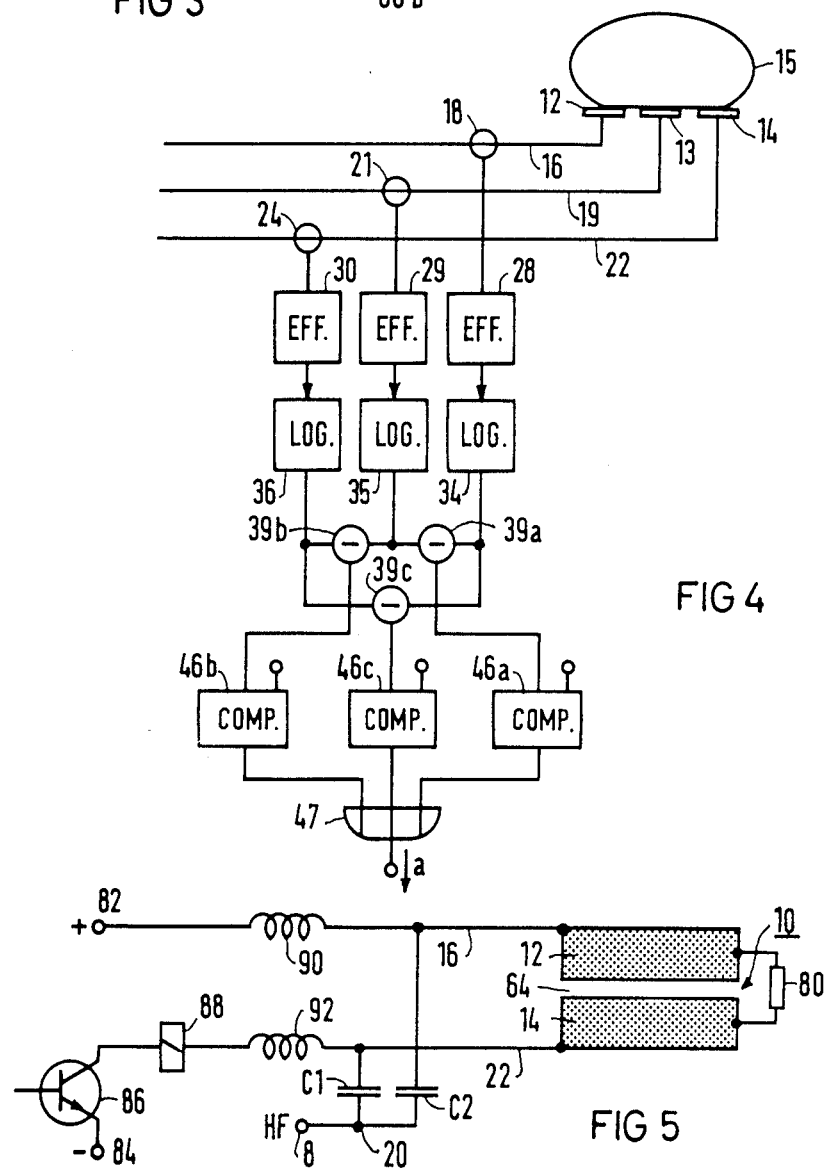
FIG. 4 illustrates a schematic of a monitoring circuit for a triple sub-divided neutral electrode constructed in accordance with FIG. 3.

A monitoring circuit operating in accordance with partial electrodes 12, 13, 14 of FIG. 3, is shown in FIG. 4. In this case current meters 18, 21 and 24 are provided for respective ones of connecting leads 16, 19 and 22. An effective value generator 28, 29 and 30 follows a respective one of each current meter in the circuit, and their output signals are individually connected to a respective one of logarithm generating elements 34, 35, 36. A difference element 39a, 39b, 39c is connected to each two of the three outputs of logarithmic elements 34, 35, 36 which may, in addition, be configured as comparators. In the example under consideration, however, individual comparators 46a, 46b, 46c are shown following the difference elements 39a, 39b, 39c in the circuit. The outputs of these comparators are connected to the three inputs of an OR-element 47. The alarm signal a, is generated at the output of OR-element 47. As in FIG. 1, this may be interconnected with an enabling signal f, through an AND-element 50 (not shown).

In the past, it has been customary to perform monitoring by employing direct current with an un-partitioned signal neutral electrode. In this approach, the direct current was delivered by a rectifier to two terminals provided on the single electrode, via a relay. In this way, it could be simply determined whether or not the electrode was connected.

Figure 5:
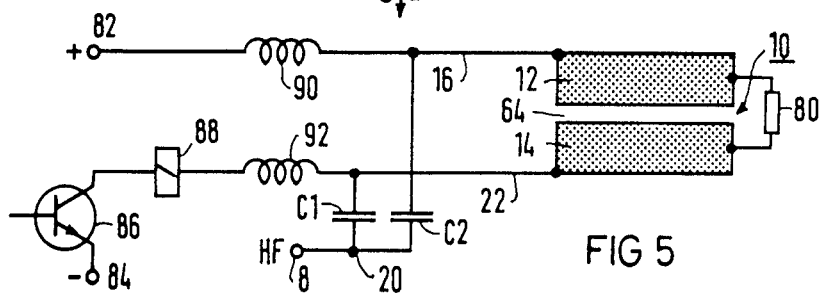
FIG. 5 illustrates a direct current monitoring circuit for a double sub-divided neutral electrode.

FIG. 5 will show clearly that it is also readily possible to employ the above-described prior art direct current monitoring circuit with a double or additionally subdivided neutral electrode 10, if electrode 10 is subject to a simple further modification. As shown in FIG. 5, the direct current is connected to terminals 16, 22 of two partial electrodes 12, 14. A resistance 80 is connected between partial electrodes 12, 14. The separating region 64 is thereby bridged by a high resistance. It is especially advantageous here to use the transition resistance Rk of the rubber film between the two segments of the neutral electrode 10 as the resistance 80. (See FIG. 2). Otherwise, the direct current circuit is of conventional design. The direct current is introduced at terminals 82, 84. A transistor 86 serves as a switch, and a relay 88, of a relatively sensitive design, may be employed for actuating protective means (not shown). Choke coils 90, 92 are connected to connecting leads 16, 22, respectively. The connecting terminal for HF-generator 2 is designated 8, as in FIG. 1.

Conventionally, an ungrounded HF-generator 2 is used and therefore neutral electrode 10 may exhibit a HF-voltage to ground. This HF-voltage must not be allowed to enter the monitoring circuits or the power supplies. Choke coils 90, 92 are placed between neutral electrode 10 and the monitoring circuits for this reason.

In prior art apparatus, when the neutral electrode is interrupted a relay (such as relay 88) actuates safety circuitry which in turn actuates an alarm signal and a cut-off of the HF-voltage. The transistor 86 is the final element of the above described monitoring electronics (behind the comparators and the timing elements). Transistor 86 interrupts the current flow to relay 88, thus performing the same functions in this apparatus design, as in the case of an interrupted neutral electrode. Hence a new monitoring circuit for neutral electrode 10 may be made a part of an existing apparatus, without the need of modifying its construction. In other words, transistor 86 and the transition resistance of neutral electrode 10 are in the quiescent current circuit of relay 88. In this way, the alarm signal is triggered either by the monitoring electronics or through the interruption of the neutral electrode. This is equivalent to the use of an OR-circuit.

Thus, there has been shown and described novel apparatus for monitoring the surface contact area of a neutral electrode which fulfills all the objects and advantages sought therefore. Many changes, modifications, variations and other uses and applications of the subject invention will, however, become apparent to those skilled in the art after considering this specification and its accompanying drawings which disclose preferred embodiments thereof. All such changes, modifications, variations and other uses and applications which do not depart from the spirit and scope of the invention are deemen to be covered by the invention which is limited only by the claims which follow.

What is claimed is:

1. A method for monitoring the neutral electrode of a HF-surgical apparatus for sufficiency of surface area contact with a body, in which the neutral electrode consists of an odd number of at least three partial electrodes and in which a comparison dependent alarm signal is generated in the event of insufficient surface area contact with said body, comprising the following steps:

applying HF-currents to three of said partial electrodes through said body;

sensing the HF-currents accepted by said three partial electrodes and forming electrical partial current signals corresponding to respective ones of said sensed accepted HF-currents;

combining three different pairs of said electrical partial current signals for developing three combined electrical signals;

comparing the level of each of said three combined electrical signals with a pre-set limit value, thereby obtaining three comparison signals;

developing a logic OR signal from said three comparison signals; and generating an alarm signal dependent upon said logic OR signal.

2. The method of claim 1, wherein said combining and comparing steps cause said logic OR signal to be representative of the ratio of said electrical partial current signals.

3. The method of claim 2, wherein said combining step comprises developing logarithms of said electrical partial current signals and then subtracting one logarithm from another.

4. The method of claim 2, wherein said generating step generates said alarm signal when the level of at least one of said three combined electrical signals exceeds said pre-set limit value.

5. The method of claim 1, wherein said combining step comprises subtracting said electrical partial current signals one from each other to develop three logic signals as said three combined electrical signals.

6. The method of claim 1, wherein said sensing and forming step develops a measurement of the effective value of each of said electrical partial current signals.

7. The method of claim 1, including the further step of monitoring at least one of said HF-currents for exceeding a level limit value and enabling the alarm signal only after the level limit value has been exceeded.

8. The method of claim 1 including the further step of time delaying said alarm signal before it is applied to actuate an alarm.

9. Circuit arrangement for monitoring the neutral electrode of a HF-surgical apparatus for sufficiency of surface contact with a body when said neutral electrode comprises an odd number of at least three partial electrodes adapted to receive said body between said partial electrodes and said active electrode, comprising:

a HF-current generator having a first and a second terminal, said first terminal for coupling said generator to said active electrode and said second terminal for coupling said generator to said neutral electrode;

current meter means for connection between each of said three partial electrodes and said HF current generator for measuring at least three partial currents developed in said at least three partial electrodes;

combining means coupled to the output side of said current meter means for combining the measured partial currents and generating at least three combined electrical signals that are a function of the combination;

a plurality of comparator means coupled to said combining means for receiving respective ones of said combined electrical signals;

a comparison element coupled to each of said comparator means for comparing respective ones of said combined electrical signals with a pre-set limit value for developing an output signal from each of said comparator means; and logic means having an input coupled to each of said comparator means for combining said output signals of said comparator means and providing at an output thereof an alarm signal.

10. A circuit arrangement according to claim 9, wherein said current meter means comprises a plurality of current transformers, one current transformer adapted to be connected to each of said partial electrodes.

11. A circuit arrangement according to claim 9, wherein an effective value generator is coupled to each current meter means for developing an effective value for the partial current developed in each partial electrode.

12. A circuit arrangement according to claim 9, wherein said combining means comprises one or more ratio generators which develop a signal level representative of the ratio of the partial currents of said partial electrodes.

13. A circuit arrangement according to claim 12, wherein each ratio generator comprises a logarithm generating element for each of the partial currents and a difference element for subtracting the logrithms of the respective partial currents.

14. A circuit arrangement according to claim 13, wherein said difference element comprises an inverter element responsive to one of the partial currents and a summing element responsive to an inverted partial current from the inverter and one non-inverted partial current.

15. A circuit arrangement according to claim 9, wherein said combining means comprises one or more difference elements, each of which develop the difference of two of said partial currents.

16. A circuit arrangement according to claim 9, further including a level comparator, one of the current meter means being connected to said level comparator for applying the partial current measured by said one current meter means as an input signal thereto, said level comparator being connected to also receive a threshold level limit value so that when the input signal exceeds the level limit value, the level comparator develops an enable signal for enabling the alarm signal.

17. A circuit arrangement according to claim 16, further including an AND element coupled to said level comparator and said logic means and responsive to said enable signal and said alarm signal, and an alarm system connected to the output of said AND element.

18. A circuit arrangement according to claim 17, wherein said alarm system includes a switch coupled to the output of said AND element for cutting-off or reducing the HF-current delivered to said active electrode and/or activating an audible or a visual alarm device.

19. A circit arrangement according to claim 18, further including a timing element coupled between said AND element and said switch for applying said alarm signal to said alarm system, which timing element delays application of said alarm signal to said alarm system.

20. A circuit arrangement for monitoring the neutral electrode of a HF-surgical apparatus for sufficiency of surface contact with a body, comprising:

an active electrode;

a neutral electrode comprising three partial electrodes and adapted to receive said body between said partial electrodes and said active electrode;

a HF-current generator having a first and a second terminal, said first terminal coupling said generator to said active electrode and said second terminal coupling said generator to said neutral electrode;

a current meter connected with each partial electrode and said second terminal for measuring partial currents developed in said partial electrodes;

a combining element coupled to the output side of each current meter for combining the measured partial currents and generating at an output a combined electrical signal that is a function of the combination;

a comparator coupled to the output of each of said combining elements for receiving a respective one of said combined electrical signals;

a comparison element coupled with each of said comparators for comparing a respective one of said combined electrical signals with a pre-set limit value for developing an output signal from each of said comparators; and logic means coupled with each of said comparators and responsive to said output signals therefrom for developing an alarm signal.

21. A circuit arrangement according to claim 20 wherein said three partial electrodes are of equal size, each being connected via a current meter of identical construction to a further terminal which is in electrical contact with said second terminal of the HF-current generator.

22. A circuit arrangement according to claim 20, wherein a resistor is connected between each of said partial electrodes.

23. A circuit arrangement according to claim 20, wherein said three partial electrodes each comprise a mesh of electrically conducting material and said meshes are laid in common upon a rubber film so that strips of said rubber film are formed between juxtaposed edges of said meshes; which strips serve as a resistance between said two partial electrodes.

* * * * *